United States Patent [19]

Fraire et al.

[11] Patent Number: 5,470,858
[45] Date of Patent: Nov. 28, 1995

[54] DERIVATIVES OF (HETERO)AROMATIC ETHERS AND THIOETHERS HAVING ANTIHYPERLIPIDEMIC ACTIVITY, PROCESS FOR THEIR PREPARATION AND PHARMACEUTICAL COMPOSITIONS CONTAINING THEM

[75] Inventors: Cristina Fraire; Massimo Bani; Ermes Vanotti; Vincenzo Olgiati, all of Milan, Italy

[73] Assignee: Pierrel SpA, Capua, Italy

[21] Appl. No.: 901,628

[22] Filed: Jun. 19, 1992

[30] Foreign Application Priority Data

Jun. 21, 1991 [IT] Italy .................. MI91A1717

[51] Int. Cl.$^6$ .................. A61K 31/52; C07H 19/20
[52] U.S. Cl. .................. 514/261; 514/263; 536/26.13; 544/265; 544/267; 544/271
[58] Field of Search .................. 514/47, 255, 366, 514/383, 394, 261, 263; 544/265, 267, 271; 536/26

[56] References Cited

U.S. PATENT DOCUMENTS 4,774,325 9/1988 Casadio et al. .................. 544/267
4,855,226 8/1989 Polito et al. .................. 544/271

FOREIGN PATENT DOCUMENTS 0175325 3/1986 European Pat. Off. .
2402672 1/1973 Germany .
6912592 9/1970 Netherlands .................. 544/271

*Primary Examiner*—Mukund J. Shah
*Assistant Examiner*—P. K. Sripada
*Attorney, Agent, or Firm*—Nikaido, Marmelstein, Murray & Oram

[57] ABSTRACT

A compound represented by the following formula I:

$$(HET)Ar-X-CH_2-Y-CH_2-O-R \qquad (I)$$

wherein:

(HET)Ar represents a bicyclic hetero aryl nucleus which is unsubstituted or is substituted;

X represents —S—;

Y represents —CO—, —C=N—$R_2$, in which $R_2$ is hydrogen or a linear or branched alkyl having 1 to 10 carbon atoms, OH, an alkoxy having 1 to 10 carbon atoms, aryloxy, arylalkoxy, —$NH_2$, —$NHCONH_2$, —$NHCSNH_2$; and R represents a phenyl substituted at para position with a carboxyl or a ($C_1$–$C_{20}$) alkoxycarbonyl group in which the alkoxy group is linear or branched.

9 Claims, No Drawings

DERIVATIVES OF (HETERO)AROMATIC ETHERS AND THIOETHERS HAVING ANTIHYPERLIPIDEMIC ACTIVITY, PROCESS FOR THEIR PREPARATION AND PHARMACEUTICAL COMPOSITIONS CONTAINING THEM

The present invention relates to novel derivatives of (hetero)aromatic ethers and thioethers having antihyperlipidemic activity, their preparation and the pharmaceutical composition containing them.

The novel derivatives according to the present invention can be represented by the following general formula I:

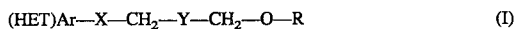

(HET)Ar—X—CH$_2$—Y—CH$_2$—O—R    (I)

wherein:

(HET)Ar represent a mono-, bi- and tri-cyclic aryl or hetero aryl nucleus possibly substituted, X represents —O— or —S—;

Y represents —CO—, a linear or branched polymethylene having 0 to 8 carbon atoms, with the proviso that it is not (CH$_2$)$_n$ in which 0<n<5 when (HET)Ar represents an imidazole ring possibly substituted with methyl and/or nitro and simultaneously X=S, —CH(OR$_1$), in which R$_1$ is hydrogen or an acyl group deriving from an aliphatic, aromatic or heterocyclic carboxylic acid, provided that R$_1$ is not hydrogen when (HET)Ar represents a guanine, adenine or adenosine group, —C=N—R$_2$, in which R$_2$ is hydrogen or a linear or branched alkyl having I to 10 carbon atoms, OH, an alkoxy having 1 to 10 carbon atoms, aryloxy, arylalkoxy, —NH$_2$, —NHCONH$_2$, —NHCSNH$_2$; and R represents a phenyl substituted at para position with a carboxyl or a (C$_1$–C$_{20}$)alkoxycarbonyl group in which the alkoxyl group may be linear or branched.

For the purpose of the present invention the wording "mono-, hi-, tri-cyclic aryl or hereto aryl nucleous possibly substituted" indicates 5 or 6 atoms membered fused heterocyclic rings containing one or more hetero atoms selected among N, O and S or aryl rings possibly bearing one to three substituents identical or different from each other.

Examples of those groups comprise phenyl, naphthyl, pyridyl, pirimidyl, pyrrolyl, oxazolyl, thiazolyl, imidazolyl, triazolyl, benzothiazolyl, benzoxazolyl, benzoimidazolyl, naphthoxazolyl, naphthothiazolyl, xanthyl, adenyl, adenosyl, guanyle and the like.

For the puposes of the present invention the term "aliphatic carboxylic acid" indicates an aliphatic carboxylic acid having linear or branched chain, saturated or unsaturated, containing 2 to 20 carbon atoms; according to a preferred feature of the invention by the above term there is meant a saturated aliphatic carboxylic acid, with linear or branched chain, containing from2 to 6 carbon atoms. Example of these acids are acetic acid, propionic acid, isobutiric acid, isoamylic acid, valeric acid, isovaleric acid and the like.

In turn the term "aromatic carboxylic acid" indicates within the present invention essentially the benzoic acid and its derivatives variously substituted on the ring, such as for example the 2-, 3-, 4-methyl-benzoic acid, 2-, 3-, 4-chlorobenzoic acid, 3,5-dimethyl-benzoic acid, 2-, 3-, 4-methoxy-benzoic acid, 3,4,5-trimethoxy-benzoic acid and the like.

The term "heterocyclic carboxylic acid" indicates the etherocyclic carboxylic acids in which the etherocyclic ring is monocyclic, contains 5 or 6 atoms of which I or 2 are heteroatoms selected among nitrogen, oxygen and sulphate; preferably by this term there are meant the positional isomers of the pridine carboxylic acid, among which more preferred are 3-pyridin carboxylic acid or nicotinic acid, pyrazin-carboxylic acid, 2-furan-carboxylic acid and the like.

A preferred group of the present invention comprises those compounds of formula I wherein X is sulphur atom and Y is as previously defined.

A more preferred group of compounds of the present invention comprises those compounds of formula (I) wherein X is a sulphur atom and Y is a carbonyl or a —CH(OR$_1$)— group, wherein the carbon atom bearing the group —OR$_1$ may exist both in the configuration R and in the configuration S.

For this reason the present invention includes both the single pure isomers and their mixtures in any proportion.

According to a particularly preferred embodiment of the present invention there are foreseen novel 8-substituted nucleoside and purine derivatives having the following formula (II) and (III)

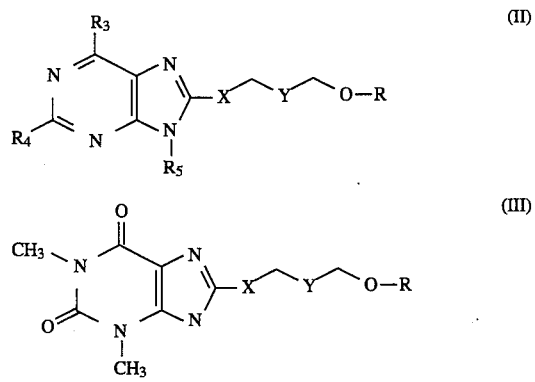

wherein R$_3$ represents an amino group or an hydroxyl group in equilibrium with the corresponding carbonyl form;

R$_4$ is a hydrogen atom or an amino group;

R$_5$ is a hydrogen atom or a β-D-ribofuranosytic radical in which both the primary hydroxyl group at 5' and the two secondary hydroxyl groups at 2' and 3' may be substituted with an acyloxy wherein the acyl derives from an aliphatic, aromatic or heterocyclic carboxylic acid, with a carbamiloxy group or with a mono-, di- or tri-phosphate group;

R is a phenyl substituted at the para position with a carboxyl group or a (C$_1$–C$_{20}$)alkoxycarbonyl group, in which the alkoxy group is linear or branched;

X is —O—, —S—

Y is —CO—, a C$_0$–C$_8$ linear or branched polymethylene, C=N—R$_2$, in which R$_2$ is as above defined.

A preferred group of the present invention comprises those compounds of formula II and III in which R$_3$ is an amino group and R$_4$ is a hydrogen atom, or R$_3$ is a hydroxyl group in (keto)enolic equilibrium, and R$_4$ is an amino group, R$_5$ in an hydrogen atom or β-D-ribofuranosil radical, in which the hydroxyl groups can be substituted as above seen, R is as previously defined and X and Y are defined as above stated.

A more preferred group of compounds of the present invention comprises those compounds of formula II and III wherein R$_3$ is an amino group, R$_4$ is hydrogen group, R$_5$ is hydrogen atom or a β-D-ribofuranosil radical in which the hydroxyl groups can be substituted as previously discussed, R is as above defined, X is sulphur atom and Y is carbonyl.

Purine derivatives variously substituted at the positions 2, 6, 8, and 9 are known in the literature, either of patent nature or different, with several pharmacological activities, for example as antiviral compounds (see for example Belgian Patent No. 833,066 and the published European applications Nos. 9154 and 85424), as bronchial-dilating agents (see for example U.S. Pat. No. 3,862,189), as antitumoral agents (see for example U.S. Pat. No. 3,238,207 and the Dutch patent application No. 67/09151) or even as hypotensive agents (see for example Dutch patent NL 8903-054 or European Patent EP 369209).

There is moreover a series of purine derivatives claiming a hypocholesterolenic activity, which are variously substituted at the positions 2, 6 and 8, but are characterized by the presence at the position 9 of a group of formula —CH$_2$—CH(OH)—CH(OH)—COOR (see for example the following japanese "Kokai": 46/39352 (corresponding to the base patent relating to eritadenine), 47/19272, 47/24039, 48/01678, 48/01679, 48/16519, 50/22039 and the Belgian Patent No. 737,949) or, of a group

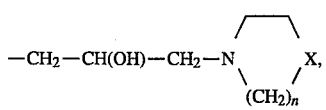

see European EP-A No. 52964.

The European Patent No. 175325 describes nucleosides and purine 8-substituted derivatives having antihyperlipidemic activity which are represented by the following general formula (IV):

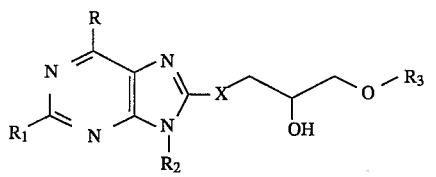

(IV)

wherein R is an amino or hydroxyl group, possibly in the tautomeric-ketonic form, $R_1$ is a hydrogen atom or an amino group, $R_2$ is a hydrogen atom or a β-D-ribofuranosyl radical wherein the primary hydroxyl group and/or the two secondary hydroxylic groups can be derivatized $R_3$ is an aryl or heteroaryl monocyclic residue possibly substituted, and X is —O— or —S—.

A general method for the preparation of the novel derivatives in which X=O, —S—, comprises the introduction of the said chain by reacting the corresponding halogen(hetero)aromatic derivative with a compound of a formula HX—CH$_2$—Y—CH$_2$—OR, wherein R is as above defined, Y is $C_0$-$C_8$ polymethylene, —CO—, —CH(OH)—, the last two ones being suitable protected and X has the above indicated meaning.

Protecting groups for the carbonyl and hydroxyl functions which have been found particularly suitable in the synthesis of the novel products of the invention, are for example respectively, ethylendioxylanyl and the cyclic ethers, particularly tetrahydropiranil, trithyl and dimethoxytrityl. The introduction of those protecting groups is generally effected according to the standard methods by using an aprotic solvent such as, for example, 1,2-dimethoxyethane, tetrahydrofurane, ethyl ether, ethyl acetate, etc, in the presence of an acid catalyst, such as for example p-toluensulphonic acid.

It is meant that the use of other protecting groups which, are not specifically indicated or discussed herein, can be well used in the process of the present invention, fall within the scope thereof.

The condensation reaction between the halogen(hetero)aromatic derivative and the compound of the formula HX—CH$_2$—Y—CH$_2$—OR is preferably carried out in an aprotic dipolar solvent such as dimethylformamide, ethers, tetrahydrofurane, dimethylsulfoxide, etc., in an aprotic apolar solvent such as toluene, xylene, etc., or in protic solvents (water, alcohols) in the presence of a suitable base such as, for example, soda, carbonates, amine bases, sodium hydride, butyllitium, phenylitium or potassium tert-butyl.

When X=S a suitable method consists in reacting the suitable mercapto(hetero)aromatic derivative with an epoxide of formula

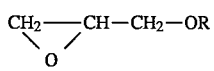

or with a ketone of formula Hal—CH$_2$—CO—CH$_2$—OR or with a halide of formula Hal—CH$_2$—(CH$_2$)$_n$—CH$_2$—Or, where Hal—Cl, Br, I, 0<n<8 and R is as above defined.

In this case the reaction is carried out in the presence of a polar, protic or aprotic organic solvent, such as alcohol, dimethylformamide, dimethylsulfoxide, etc. preferably in the presence of a basic catalyst substantially selected in the class of the sterically hindered tertiary amines, such as trialkylamines, 2,6-lutidine, piridyne, etc. The reaction is preferably carried out at room temperature even if sometimes it can be convenient to slightly speed up the reaction at temperature of between the room temperature and 100° C. and preferably to the reflux temperature of a low alcohol, such as ethanol or hisopropanol.

The reaction is generally completed after a time interval varying between 1 and 24 hours depending on the substrate and of the possibly used catalyst.

At the end of the reaction the crystallized product is filtered or the solvent is removed and the residue is purified according to the classic methods of crystallization from suitable solvents and possibly from their mixture by chromatography.

In the case of the compound of formula II and III the general method for the preparation of the novel derivatives in which X=—O—, —S— consists in the introduction of the said chain at the 8 position by reacting the corresponding 8-bromo substituted purine or nucleoside derivative with a compound of formula HX—CH$_2$—Y—CH$_2$—Or, wherein R and Y have the meaning above indicated and X has the above mentioned meaning.

When X represents an oxygen atom the free hydroxyl groups and preferably also the possibly present amino groups on the starting purine substrate must be protected in order to avoid competing reactions or the substrate the activation.

Protecting groups for the hydroxyl functions which have been found particularly suitable in the synthesis or the novel product of the invention are, for example, the cyclic ethers and particularly tetrahydrophinyl, trithyl and dimethoxytrityl.

The introduction of these protecting groups is generally effected according to the standard method by using an aprotic solvent such as for example 1,2-dimethoxyethane, tetrahydrofuran, ethylic ether, ethyl acetate, etc., in presence of an acidic catalyst, such as for example p-toluenesulphonic.

When, on the contrary, it is desired to simultaneously protect the two hydroxyl groups at 3' and 4', it is preferred to react the purine substrate with acetone and an hydros p-toluensulphonic acid, whereby the vicinal diol of the ribosyl is converted into the corresponding acetonide.

Reactants which are well useful in the process of the present invention for the protection of the amino group are the silyl derivatives and particularly the halides of trimethylsilyl or dimethyl-t-butilsilyl and the dimethylacetal of dimethylformamide. The latter compound is particularly preferred since the protection obtained by reacting the purine base with the dimethylacetal of dimethylformamide in dimethylformamide gives place to almost quantitative yields and is of easy use.

It is meant that the use of other protecting groups both for the hydroxyl functions and of the aminic ones, which although being not specifically indicated or discussed herein can be well used in the process of the present invention, fall in the scope thereof.

The condensation reaction between the 8-bromo purine or nucleoside derivative possibly protected and the compound of formula HX—CH$_2$—Y—CH$_2$—OR is preferably carried out in an aprotic dipolar solvent such as dimethylformamide, ethers, tetrahydrofurane, dimethylsuiphoxide, etc., in an aprotic apolar solvent such as toluene, xylene, etc., or in protic solvents (alcohols, water) in the presence of a suitable base such as, for example, soda, carbonates, aminic bases, sodium hydride, butyllitium, phenyllitium or potassium tert-butyl.

The pattern of the reaction is monitored by means of the standard chromatographic methods (HPLC, TLC) and at the end thereof the obtained product is isolated and the possible protecting groups are removed.

A convenient method permitting the simultaneous removal both of the protecting groups for the hydroxyl functions and of the protecting groups for the aminic functions is the acidic hydrolyses with diluted sulphuric acid at room temperature in aqueous or alcoholic solvent or with hot-p-toluensulfphonic acid.

As regards the purification of the desired product, which can be carried out both before and after the protections step, suitably useful methods are the standard method of crystallization from proper solvents and the chromatographic methods (column chromatography or preparation HPLC)

When X=S an alternative method consists in reacting an 8-mercapto purine derivative, which can be readily obtained, for example, by reacting the corresponding 8-bromo derivative with sodium sulphydrate in aqueous environment or with hydrogen sulphide in a basic organic solvent with a ketone of formula Hal—CH$_2$—CO—CH$_2$—OR or with a halyde of formula Hal—CH$_2$—(CH$_2$)$_n$—CH$_2$—OR, wherein Hal=Cl ,Br, I, 0<n<8 and R is as above defined.

In this case the reaction is carried out in the presence of a polar, protic or aprotic organic solvent, such as alcohol, dimethylformamide, dimethylsulfoxide, etc., preferably in the presence of a basic catalyst essentially selected in the class of the sterically hindered tertiary amine such as trialkylamine, 2,6-lutidine, piridyne.

The reaction is preferably effected at the room temperature even if sometimes it can be convenient to slightly speed up its behaviour at temperature of between the room temperature and 100° C. and preferably at the reflux temperature of an alcohol such as ethanol or isopropanol.

The reaction is generally completed after a time interval which can vary from 1 to 24 hours depending on the substrate and on the possibly used catalyst.

At the end of the reaction the crystallized product is filtered or the solvent is removed and the residue is purified according to the classic methods of crystallization from suitable solvents or possibly from their mixture or by chromatography.

The compounds in which Y=C=NR$_2$, are obtained from the compounds which is Y=—CO—, by means of the typical reactions of carbonyl conversion.

Likewise, some compounds of formula I can be prepared by chemical conversion of other compounds also falling in the same formula I.

For example the compounds having a carboxyl group as the R substituent can be prepared by basic hydrolyses of the corresponding compounds having an alkoxycarbonyl group and in turn may be reacted with different alcohol or with amines to get different esters or amides.

When it is desired to obtain a compound of formula II in which only the primary hydroxy group is esterified or it is esterified differently from the two secondary hydroxy groups, it is necessary to block the two secondary hydroxyls with a protecting group which is readily removable at the end of the reaction, then derivatize the primary hydroxy group and lastly restore the two free secondary hydroxyls which, in turn, may be suitably reacted, if desired.

Preferably the protection of the two secondary hydroxyls is effected on the purine base before the introduction of the bromine atom and of the substitution thereof with the —SH group, whereas the derivatization of the primary hydroxyl is effected after the introduction of the mercapto group and the deprotection of the two secondary hydroxyls can be carried out both before and after the introduction of the chain at 8.

More specifically the compounds of the present invention can be synthetized as follows:

1. The products characterized by X=—O— and Y=—CH(OR$_1$)— are synthetized from the proper halogen-(hetero)aromatic derivatives by reaction with the alcohol of formula HO—CH$_2$—CH—[O(prot)]—CH$_2$—O—R, wherein "prot" is a suitable group protecting the hydroxy function (for example tetrahydropyranyl, etc.) which can be readily removed at the end of the reaction. This hydroxy function may be acylated according to standard literature methods.

The alcohol in turn can be prepared from the analogous halogen derivative obtainable by adding the halogenide to the epoxide, either racemic or optically active, having the formula:

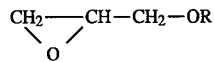

2. The compounds wherein X=—O— and Y=—CO are prepared by reaction of the suitable halogen(hetero)aromatic derivatives with the protected hydroxyketone having the formula HO—CH$_2$—C(prot)—CH$_2$—OR, in which "prot" is a suitable protecting group such as for example ethylendioxolanyl, which can be obtained from the analogous halogen derivative of formula Hal—CH$_2$—C(prot)—CH$_2$—OR, wherein Hal=Cl, Br, I, the latter being in turn preparable from the haloketone Hal—CH$_2$—CO—CH$_2$—OR, which can be synthetized by oxidation, according to standard methods, of the corresponding haloalcohol prepared by adding the halogenide to the epoxide, either racemic or optically active having the formula

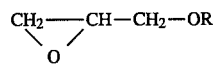

Alternatively these compounds can be prepared by reacting the suitable hydroxy-(hetero)aromatic compounds with the above described halogen derivative.

3. The compounds in which X=—O— and Y=—(CH$_2$)—, wherein 0<n<8, are prepared by reacting the proper halogen-(hetero)aromatic derivatives with the alcohol of formula HO—CH$_2$—(CH$_2$)$_n$—CH$_2$—OR, which can be obtained from the like halogen derivative which in turn can be synthetized by reacting the dihalogen derivative of formula Hal—CH$_2$—(CH$_2$)$_n$—CH$_2$—Hal, wherein Hal = Cl, Br, I, with R—OH according to standard literature methods.

The dihalogen derivatives are mostly commercially available or can be prepared by conventional methods.

4. The derivatives in which X=—S— and Y=—CH(OR$_1$)— are obtained by the reaction of the proper mercapto-(hetero)aromatic compound with the epoxide, either racemic or optically active, having the formula:

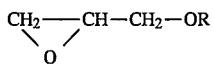

The hydroxy group (R$_1$=H) can be possibly acylated according to literature standard methods. Alternatively these derivatives can be prepared by reacting the suitable halogen-(hetero)aromatic derivatives with HS—CH$_2$—CH(OR$_1$)—CH$_2$OR which in turn can be obtained from the corresponding halide described at the paragraph 1 above.

5. The products in which X=—S— and Y=—CO— are synthetized by reacting the proper mercapto-(heteroaromatic derivative with the haloketone described at the paragraph 2 above. Alternatively the preparation can take place from the suitable halogen-(hetero)aromatic derivative by reaction with mercaptoketones of formula HS—CH$_2$—CO—CH$_2$OR, in turn obtainable from the corresponding haloketone described at the paragraph 2 above.

6. The derivatives in which X=—S— and Y=(CH$_2$)$_n$—, wherein 0<n<8, are prepared from a proper mercapto-(hetero)aromatic derivative by reaction with the halogen derivative described at the paragraph 3 above.

7. The compounds having X=—O— and Y=C=N—R$_2$, wherein R$_2$ is H, a C$_1$-C$_{10}$ linear or branched alkyl, —OH, a C$_1$-C$_{10}$ alkoxy, aryloxy, arylalkoxy, —NH$_2$, —NHCONH$_2$, —NHCSNH$_2$, are prepared from the compounds described at the paragraph 2 above according to the, conventional methods for the derivatization of carbonyls.

8. The compounds having X=—S— and Y=C=N—R$_2$, wherein R$_2$ is H, a C$_1$-C$_{10}$ linear or branched alkyl, —OH, a C$_1$-C$_{10}$ alkoxy, aryloxy, arylalkoxy, —NH$_2$, —NHCONH$_2$, —NHCSNH$_2$, are prepared from the compounds described at the paragraph 5 above according to the conventional methods for the derivatization of carbonyls.

The following examples detailedly describe some compounds of the present invention and the process for their preparation, but it shall never be construed as a limitation of the scope of the invention.

EXAMPLE 1

2-[3-[(p-isobutyloxycarbonyl)-phenoxyl]-2-oxo-propylthio]-benzoxazole

The suspension of 2-mercapto-benzoxazole (13.4 mmoles) in absolute ethanol (40 ml) is added with 2,6-lutidine (1.8 ml, 16 mmoles) and with a solution of isobutyl p-(3-bromo-2-oxo)-propyloxy benzoate (13.4 mmoles) in absolute ethanol (40 ml), by stirring at room temperature. The reaction is completed after 1 hour with the precipitation of the product. The reaction product is filtered, washed with ethyl ether and crystallized from ethyl acetate/petroleum ether. The thus obtained solid, with a yield of 90%, has m.p. of 106°–108° C.

By following the conditions described in the example 1 the following products are synthesized:

EXAMPLE 2

2-[3-[(p-isobutyloxycarbonyl)phenoxy]-2-oxo-propylthio]-benzothiazole

From 2-mercapto-benzothiazole, yield 78%, m.p. 85°–86° C.

EXAMPLE 3

8-[3-](p-isobutyloxycarbonyl)phenoxy]-2-oxo-propylthio]-thiophylline

From 8-mercapto-theophylline, yield 77%, m.p. 191°–192° C.

EXAMPLE 4

1-methyl-2-[3-[(p-isobutyloxycarbonyl)-phenoxy]-2-hydroxy-propylthio]-imidazole hydrochloride The suspension of 5.73 g (50 mmoles) of 1-methyl-2-mercapto-imidazole in absolute ethanol (100 ml) is added with 2,6-lutidine in catalytic amount and there is dropwise added the solution of isobutyl p-(2,3-epoxy)-propyloxybenzoate (12.5 g; 50 mmoles) in absolute ethanol (50 mmoles) at room temperature under stirring. The mixture is heated to reflux for 6 hours. The solvent is evaporated under vacuum, the residue is taken with ethyl acetate and washed with aqueous saturated solution of sodium bicarbonate and with water. The mixture is made anhydrous over anhydrous sodium sulfate and concentrated to an oil.

The lutidine is completely removed by evaporation under vacuum. The product, dissolved in acetone, is treated with an excess of 37% aqueous hydrochloric acid and maintained under stirring until the salification is completed. The mixture is concentrated to dryness under vacuum with subsequent additions of toluene/ethanol, the solid is comminuted with ethyl ether/hexane and is crystallized from a mixture of acetone/ethyl acetate. The product is obtained with a yield of 64% and has melting point 104°–108° C.

By repeating the operating method of example 4 the following derivatives are prepared:

EXAMPLE 5

2-[3-[(p-isobutyloxycarbonyl)-phenoxy]-2-hydroxy-propylthio]-pirimidine hydrochloride From 2-mercapto-pirimidine, yield 60%, m.p. 115°–116° C.:

EXAMPLE 6

2-[3-[(p-isobutyloxycarbonyl)-phenoxy]-2-hydroxy-propylthio]-benzothiazole

From 2-mercapto-benzothiazole, yield 80%, m.p.95%.

EXAMPLE 7

2-[3-[(p-carboxy)-phenoxy]-2-hydroxy-propylthio]-benzothiazole

From 2-mercapto-benzothiazole and from p-(2,3-epoxy)-propyloxybenzoic acid, yield 60%, m.p. 141° C.

EXAMPLE 8

2-[3-[(p-ethyloxycarbonyl)-phenoxy]-2-hydroxy-propylthio]-benzothiazole

From 2-mercapto-benzothiazole and ethyl p-(2,3-epoxy)-propyloxybenzoate, yield 65%, m.p. 80° C.

EXAMPLE 9

2-[3-[(p-isobutyloxycarbonyl)-phenoxy]-2-hydroxy-propylthio]6-ethoxy-benzothiazole From 2-mercapto,6-ethoxybenzothiazole,, m.p. 92°–93° C.; yield 87%.

EXAMPLE 10

2-[3-[(p-isobutyloxycarbonyl)-phenoxy]-2-hydroxy-propylthio]5-chloro-benzothiazole From 2-mercapto,5-chloro-benzothiazole, m.p. 67°–70° C., yield 88%.

EXAMPLE 11

2-[3-[(p-isobutyloxycarbonyl)-phenoxy]-2-hydroxy-propylthio]-benzothiazole

From 2-mercapto-benzoxazole, yield 59%, m.p. 85°–87° C.

EXAMPLE 12

2-[3-[(p-isobutyloxycarbonyl)-phenoxy]-2-nicotinoyloxy-propylthio]-benzothiazole From 2-[3-[(p-isobutyloxycarbonyl)-phenoxy]-2-hydroxy-propylthio]-benzoxazole, yield 80%, oil.

EXAMPLE 13

2-[3-[(p-ethyloxycarbonyl)-phenoxy]-2-hydroxy-propylthio]-benzothiazole

From 2-mercapto-benzoxazole and from ethyl p-(2,3-epoxy)-propyloxybenzoate, yield 52%, m.p. 62°–64° C.

EXAMPLE 14

1-methyl-2-[3-[(p-isobutyloxycarbonyl)-phenoxy]-2-hydroxy-propylthio]-benzimidazole From 1-methyl-2-mercapto-benzimidazole, yield 79%, m.p. 90°–91° C.

EXAMPLE 15

2-[3-[(p-isobutylcarbonyl)-phenoxy]-2-hydroxy-propylthio]-napht[2,3-d]oxazole

From 2-mercapto-napht[2,3-d]oxazole, yield 53%, m.p. 101°–102° C.

EXAMPLE 16

2-[3-[(p-isobutylcarbonyl)-phenoxy]-2-hydroxy-propylthio]-4,5-diphenyl-oxazole

From 4,5-diphenyloxazol-2-thione, yield 65%, m.p.48°–50° C.

EXAMPLE 17

2-[3-[(p-isobutylcarbonyl)-phenoxy]-2-hydroxy-propylthio]-4,5-diphenyl-imidazole From 4,5-diphenylimidazo-2-thione, yield 87%, m.p. 135°–138° C.

EXAMPLE 18

2-[3-[(p-isobutylcarbonyl)-phenoxy]-2-hydroxy-propylthio]-benzimidazole

From 2-mercapto-benzimidazole, yield 55%, m.p. 121°–124° C.

EXAMPLE 19

2-[3-[(p-isobutylcarbonyl)-phenoxy]-2-hydroxy-propylthio]-1,3,4-triazole sodium salt From 2-mercapto-1,3,4-triazole, m.p.75° C., yield 91%

EXAMPLE 20

4-[3-[(p-isobutylcarbonyl)-phenoxy]-2-hydroxy-propylthio]-pyridine

From 4-mercapto-pyridine, yield 60%, m.p.100°–102° C.

EXAMPLE 21

2-[3-[(p-isobutylcarbonyl)-phenoxy]-2-hydroxy-propylthio]-pyridine

From 2-mercapto-pyridine, yield 85%,m.p.55°–56° C.

EXAMPLE 22

8-[3-[(p-isobutylcarbonyl)-phenoxy]-2-hydroxy-propylthio]-caffein

From 8-mercapto-caffein, m.p. 126°–128° C.,yield 80%

EXAMPLE 23

7-methoxymethyl-8-[3-[(p-isobutyloxycarbonyl)-phenoxy]-2-hydroxy-propylthio]-theophilline From 7-methoxymethyl-8-mercapto-theophilline, m.p. 101°–103° C., yield 74%

EXAMPLE 24

8-[3-[(p-isobutylcarbonyl)-phenoxy]-2-hydroxy-propylthio]-theophilline

From 8-mercapto-theophilline, yield 63%, m.p. 140°–142° C.

EXAMPLE 25

8-[3-[(p-isobutylcarbonyl)-phenoxy]-2-hydroxy-propylthio]-adenosine

The suspension of 8-mercapto-adenosine (5.4 g, 18 mmoles) in isobutanol (150 ml) is added with 11.9 ml of 1.52M sodium isobutoxide (18 mmoles), under stirring and in anhydrous condition.

The mixture is heated to 60° C. and dropwise added with the solution of isobutyl p-(3-bromo)-propyloxy benzoate (8.2 g, 26 mmoles) in isobutanol (35 ml) and the mixture is stirred for 3 hours at 60° C. and overnight at room temperature.

The salts are separated by filtration and the solvent is completely evaporated under vacuum. The residue is taken with ethyl acetate (200 ml), and the organic phase is washed firstly with an aqueous saturated solution of sodium bicarbonate (200 ml) and then with water (200 ml). The organic phase is made anhydrous over anhydrous sodium sulfate and concentrated to an oil, which is crystallized from absolute ethanol; the product, obtained with a yield of 70%, has m.p.174°–175° C.

EXAMPLE 26

8-[5-[(p-isobutylcarbonyl)-phenoxy]-2-hydroxy-propylthio]-adenosine

Example 25 is repeated starting from isobutyl p-(5-bromo)-pentyloxybenzoate.

The product having m.p. 142° C., is obtained with a final yield 75%.

EXAMPLE 27

8-[2-[(p-isobutylcarbonyl)-phenoxy]-ethylthio]-adenosine

Example 25 is repeated starting from isobutyl p-(5-bromo)-ethoxybenzoate.

A solid having m.p.128° C., is obtained with a yield 47%.

EXAMPLE 28

8-[3-[(p-isobutylcarbonyl)-phenoxy]-2-oxo-propylthio]-adenosine

The suspension of 8-mercapto-adenosine (4 g, 13.4 mmoles) in 40 ml of absolute ethanol is added with 2,6-lutidine (16 mmole, 1.8 ml) and with the solution of isobutyl p-(5-bromo-2-oxo)-propyloxybenzoate (4.4 g, 13.4 mmoles) in 40 ml of absolute ethanol. The mixture is heated to reflux for 3 hours. The solvent is completely removed under vacuum, and the, residue is taken with ethyl acetate (150 ml), and washed with an aqueous saturated solution of sodium bicarbonate and then with water. The organic phase is made anhydrous over sodium sulfate and the solvent and the residual 2,6-lutidine are removed completely by evaporation under vacuum. The raw solid is comminuted in ethyl ether, filtered and crystallized from absolute ethanol.

The product, obtained with a yield of 85%, has m.p.162°–164° C.

By repeating the operating method of example 28 the following derivatives are prepared:

EXAMPLE 29

8-[3-[(p-carboxy)-phenoxy]-2-oxo-propylthio]-adenosine

From p-(3-bromo-2-oxo)-propyloxybenzoic acid.

Yield 59%, m.p.195° C.

EXAMPLE 30

8-[3-[(p-isobutylcarbonyl)-phenoxy]-2-oxo-propylthio]-adenine

From 8-mercapto-adenine and isobutyl p-(3-bromo-2-oxo)-propyloxybenzoate.

Yield 80%, m.p. 184° C.

EXAMPLE 31

8-[3-[(p-isobutylcarbonyl)-phenoxy]-2-hydroxyimino-propylthio]-adenosine

A suspension in isobutanol containing 8-[3-[(p-isobutylcarbonyl)-phenoxy]-2-oxo-propylthio]-adenosine (27.45 mmoles), imidazole (164.7 mmoles) and hydroxylamine hydrochloride (137.25 mmoles) is heated to 100° C. for 10 minutes. The solvent is stripped with n-heptane, the residue is taken with ethyl acetate (500 ml), and washed with aqueous saturated solution of sodium bicarbonate and then of sodium chloride. The mixture is made anhydrous on sodium sulfate and concentrated under vacuum.

The raw product is crystallized from acetone/n-heptane, and washed with diethyl ether. A solid is obtained having m.p.156°–160° C., with yield of 90%.

EXAMPLE 32

8-[3-[(p-isobutylcarbonyl)-phenoxy]-2-methoxyimino-propylthio]-adenosine

By repeating the operating method of example 31 a solid is obtained with m.p. 104°–106° C. and yield 72%

EXAMPLE 33

8-[3-[(p-isobutylcarbonyl)-phenoxy]-2-hydrazonecarboxamide-propylthio]-adenosine A solution in ethanol ( 100 ml) of 8-[3-[(p-isobutyloxycarbonyl)-phenoxy]-2-oxo-propylthio]-adenosine (18.3 mmoles) is added with a solution of semicarbazide (18.3 mmoles) in a mixture of ethanol (100 ml), water (10 ml) and 35% HCl (5 ml).

The mixture is stirred at room temperature for 3 hours and the precipitated solid is filtered. Yield 88%, m.p. 185° C.

EXAMPLE 34

8-[3-[(p-isobutylcarbonyl)-phenoxy]-2-(R)-hydroxy-propylthio]-2',3'-O-isopropyliden-adenosine From 8-[3-[(p-isobutyloxycarbonyl)-phenoxy]-2-(R)-hydroxy-propylthio]-adenosine and acetone.

Yield 75%, m.p. 75°–77° C.

EXAMPLE 35

8-[3-[p-(2,3-dihydroxy-propyloxycarbonyl)-phenoxy]-2-hydroxy-propylthio]-adenosine From 8-mercapto-adenosine and p-(2',3'-O-isopropyliden-propyloxycarbonyl)-phenoxy-2,3-epoxypropane.

Yield 55%, m.p. 132°–134° C.

EXAMPLE 36

8-[3-[(p-carboxy)-phenoxy]-2-oxo-propylthio]-adenine

From 8-mercapto-adenine and p-(2-oxo,3-bromo propyloxy)-benzoic acid.

Yield 75%, m.p.196°–198° C.

EXAMPLE 37

4 -[3 -[(p-isobutoxycarbonyl)-phenoxy]-2-hydroxy-propylthio]-2,6-di-t-butyl-phenol From 3,5-di-t-butyl,4-hydroxy-thiophenol and p-isobutoxycarbonyl-phenoxy-2,3-epoxypropane Yield 82%,m.p.82°–85° C.

EXAMPLE 38

2-[3-[(p-carboxy)-phenoxy]-2-oxo-propylthio]-benzothiazole

From 2-mercapto-benzothiazole and isobutyl p-(3-bromo-2-oxo)-propoxybenzoate.

Yield 51%, m.p.181°–185° C.

EXAMPLE 39

2-[3-[(p-carboxy)-phenoxy]-2-oxo-propylthio]-benzoxazole

From 2-mercapto-benzoxazole and isobutyl p-(3-bromo-2-oxo)-propoxybenzoate.

Yield 70%, m.p. 180°–184°

EXAMPLE 40

2-[5-(4-isobutyloxycarbonylphenoxy)-pentyloxy]-benzimidazole

A solution of 2-hydroxybeazimidazole (8.8 mmoloes) in anhydrous dimethylformamide (DMF) (12 ml) is dropwise added, at room temperature and under vacuum, to a suspension of sodium hydride (10 mmoles) in anhydrous DMF (2 ml).

Ten minutes after the end of the dropwise addition, a solution of isobutyl 4-(5-bromopentyloxy)benzoate (8.8 mmoles) in anhydrous DMF (2 ml) is dropwise added.

The resulting mixture is stirred at room temperature for 3 hours and then for 1 hour at 50° C.

The mixture is diluted with water, extracted (×3) with ethyl acetate, made anhydrous on anhydrous sodium sulfate and concentrated under vacuum. The raw product is purified by column chromatography. The desired product is obtained as a white solid, m.p.89° C.

The compounds of the present invention are characterized by a hypolipemizing activity. This activity takes place through the reduction of the plasma concentration of the total cholesterol as the result of the diminution of the very low density lipoproteins (VLDL) and low density lipoproteins (LDL) as well as of the simultaneous increase of the high density lipoproteins (HDL). To these effects on the different cholesterol fractions a hypotriglyceridemizing activity.

The lipoproteins are circulating complexes consisting of plasma lipids, including cholesterol and triglycerides, and of particular proteins, called apoproteins, which are peculiar for each lipoprotein. The main classes of these lipoproteins are different according to chemical physical properties and their increase invariably causes a hyperlipemia.

The hyperlipoproteinaemie are conditions in which the concentration of lipoproteins carrying on the cholesterol and the triglycerides in the plasma exceeds the normal limits and are the biochemical evidence of a number of pathologies differing as regards the etiology, symptomatology, prognosis and therapeutical response. As a matter of fact the classification of the several lipidic disorders on the basis of the analysis of the haematic lipoproteins has lead to the characterization of different clinical pictures. A number of clinical studies has permitted to establish a relationship between particular liproteic classes and clinical evidences of atherosclerosis. More particularly evidences have been found of a positive relationship between the LDL cholesterol plasma concentration and the development of coronary diseases, as well as of a negative relationship between the levels of HDL cholesterol and the risk of coronary pathologies (Circulation, 80, 1989, pag. 719–723).

Likewise the LDL cholesterol, also high plasma concentrations of triglycerides are reported as a risk parameter for the atherosclerosis development (Drugs, 40 (Suppl. 1).1990, pag. 38–41).

From all the above considerations it is evident that a hypolipemizing compound capable of reducing both the concentration of the LDL+VLDL fraction of cholesterol as well as the triglycerides concentration and simultaneously increase the plasma levels of the HDL fraction of cholesterol is to be considered as an agent endowed with a remarkable therapeutical potentiality in the treatment of hyperlipaemia.

The hypolipemizing activity of the compounds of the present invention has been evaluated in the rat using SD male animals (Charles River) of an initial weight of 150 g, housed in controlled environment at a temperature of 21°±1° C., relative humidity 60% and a 12 hours light/dark cycle.

Experimental models have been used in which the animals are rendered hiperlipaemic by "ad libitum" food administration with a modified Nath diet (Atherosclerosis 30, 1978, pag. 45–46) having the following composition:

| hydrogenated coconut oil | 24% |
|---|---|
| cholesterol | 1% |
| cholic acid | 1% |
| casein and vitamins | 20% |
| mineral salts | 4% |
| corn oil | 1% |
| sucrose | 49% |

In the first model the animals have been fed with this diet for 5 consecutive days, during which they received the pharmacological treatment once a day by oral route and were sacrificed 2 hours after the last administration.

At the time of the sacrifice the blood was removed, for the lipid determination, as well as the liver the weight of which was the index of a possible hepatomegaly.

By this experimental model the concentration of the serum lipids attained very high values which, in the control group, was four times the normal values for the total cholesterol and the triglycerides.

In the second model a diet was used which was modified with respect to the former one by the following parameters:

| cholesterol | 0.5% |
|---|---|
| cholic acid | 0.5% |
| casein and vitamins | 21.0% |

The animals were fasted with this diet for 15 days consecutively, during which they received the pharmacological treatment once a day by oral route and were sacrificed 24 hours after the last administration. At the sacrifice time the blood was removed for the lipid determination and the liver was removed as well to be weighed and used for the evaluation of the catalase enzyme as the index of the peroxysomes proliferation and thus of hepatotoxicity.

This experimental model has been used only for the molecules which in the first model were found more promising, and has permitted to get values of the serum lipids from 2 to 3 times higher than the normal values both for the total cholesterol and for the triglycerides.

This experimental model was used to:
a) evaluate the effectiveness on a less marked hyperlipoproteinaemy, and
b) assess mainly at the hepatic level the tolerability of the compounds during a more extended treatment.

The determination of the triglycerides, of the total cholesterol and of the cholesterol associated to the HDL has been effected by means of a commercial enzymatic kit. The concentration of the cholesterol associated to VLDL+LDL has been determined by difference between total cholesterol and HDL.

The results obtained in the experimental model of the 5 days duration for some compounds representative of the invention are reported in the following table 1. The data are expressed as percent variation with respect to the hyperlipaemic controls to which carboxymethylcellulose as 0.5% in water at the dose of 10 ml/kg/day by oral route was administered. The same vehicle was used for the suspension of the tested compounds at the doses of 100 and 300 mg/kg/day by oral route.

On the basis of the indications provided by this screening the most interesting compounds have been evaluated by the 15 days experimental model which permits both the evaluation of the effectiveness in the case of a hyperlipaemia less marked and more constant, and the tolerability control of the compounds during a longer term treatment.

In this case too the results (reported in the following table 2) are expressed as the percent variation with respect to the hyperlipaemic controls to which carboxymethylcellulose as 0.5% in water was administered by oral route at the dose of 10 ml/kg/day. The same vehicle was used for the suspension of the compounds being tested, administered at the doses; of 50 and 100 mg/kg/day by oral route.

In order to evaluate the hepatic tolerability of the compounds of interest they have been administered for 15 days at a high dose (300 mg/kg/day) according to the same conditions of the previous experiment. 24 hours after the last treatment the animals have been sacrificed, and the liver has been removed and stored at −20° C. up to the time of dosing the activity of the catalase enzyme (Methods of enzymatic analysis, vol.2, pag. 673, 1974 edit. H. U. Bergmeyer, Verlag Chemie International).

The results are reported in the following table 3 as absolute values.

TABLE 1

| Example n° | Dose mg/kg | Triglycerides | Total cholesterol | Cholesterol HDL | Cholesterol VLDL + LDL | Hepatic index* |
|---|---|---|---|---|---|---|
| 1 | 100 | −27,6 | −5,7 | +2,6 | −6,1 | −8,5 |
|  | 300 | −18,4 | −5,2 | +17,9 | −6,4 | −2,5 |
| 2 | 100 | −22,1 | −13,2 | +10,4 | −14,7 | −6,5 |
|  | 300 | −32,5 | −19,5 | +13,9 | −21,8 | −1,6 |
| 3 | 100 | −6,5 | −1,1 | +11,7 | −1,3 | +3,2 |
|  | 300 | −5,8 | −10,5 | +3,5 | −10,7 | −1,5 |
| 4 | 100 | −5,9 | +7,7 | −3,4 | +9,2 | +2,2 |
|  | 300 | +0,2 | −2,6 | +8,2 | −4,0 | +4,3 |
| 5 | 100 | +13,8 | +22,3 | −17,7 | +24,0 | −4,1 |
|  | 300 | −14,9 | −20,3 | −8,5 | −20,7 | −5,7 |
| 6 | 100 | −15,6 | −17,0 | +7,7 | −18,8 | +2,2 |
|  | 300 | −23,4 | −24,9 | +17,6 | −27,9 | +0,4 |
| 9 | 100 | +0,9 | +1,0 | +2,4 | +0,9 | −0,8 |
|  | 300 | +2,8 | −6,5 | −0,2 | −7,0 | −1,2 |
| 10 | 100 | −8,5 | −18,6 | +5,5 | −20,4 | −2,2 |
|  | 300 | −26,3 | −23,3 | +17,3 | −26,4 | −0,6 |
| 11 | 100 | −21,6 | −21,4 | +9,5 | −22,8 | −2,3 |
|  | 300 | −30,3 | −37,1 | +14,9 | −39,7 | −1,7 |
| 12 | 100 | −19,0 | +11,6 | +12,5 | +11,5 | −3,9 |
|  | 300 | −39,4 | −7,8 | +8,6 | −8,9 | −10,8 |
| 15 | 100 | +5,0 | +16,5 | +0,8 | +17,6 | −2,6 |
|  | 300 | +5,2 | −8,2 | +13,4 | −9,8 | +0,6 |
| 16 | 100 | −34,4 | −17,8 | +2,9 | −20,5 | −1,2 |
|  | 300 | −49,6 | −32,8 | −22,5 | −34,7 | +3,0 |
| 18 | 100 | −19,0 | +1,0 | +3,2 | +0,2 | +3,8 |
|  | 300 | −13,1 | +9,1 | +6,5 | +9,0 | +3,9 |
| 19 | 100 | −2,4 | −5,3 | −5,5 | −5,2 | −12,7 |
|  | 300 | −8,3 | −3,4 | −9,3 | −2,8 | +5,0 |
| 20 | 100 | −16,2 | +17,3 | −12,6 | +18,5 | −12,3 |
|  | 300 | −18,4 | −8,3 | −21,8 | −7,7 | −7,9 |
| 21 | 100 | +31,9 | +24,8 | +1,3 | +27,2 | +11,5 |
|  | 300 | −19.5 | +6,7 | +31,9 | +4,1 | +5,6 |
| 22 | 100 | −23,1 | +16,0 | −1,2 | +17,7 | −7,1 |
|  | 300 | −12,4 | +19,7 | −10,3 | +21,7 | −0,9 |
| 24 | 100 | −26,0 | −14,7 | +9,8 | −15,8 | +0,6 |
|  | 300 | −17,5 | −15,2 | +13,0 | −16,5 | −3,0 |
| 25 | 100 | −3,3 | −9,7 | −1,2 | −10,0 | −1,1 |
|  | 300 | +15,7 | −5,2 | −7,1 | −4,8 | −2,8 |
| 27 | 100 | −0,4 | −13,6 | +0,1 | −14,6 | +0,8 |
|  | 300 | −10,2 | −18,4 | +5,7 | −19,3 | +0,7 |
| 28 | 100 | −16,3 | −14,0 | +5,7 | −15,1 | −2,8 |
|  | 300 | −22,5 | −31,3 | +22,7 | −33,7 | −5,5 |
| 31 | 100 | +14,7 | −0,3 | +3,2 | −6,6 | +3,6 |
|  | 300 | −0,7 | −24,7 | −5,1 | −25,7 | −1,5 |
| 32 | 100 | −7,2 | −14,3 | +31,7 | −16,7 | −2,5 |
|  | 300 | −2,6 | +3,0 | −1,7 | +3,3 | +3,1 |
| 33 | 100 | −27,8 | −34,8 | +22,2 | −37,4 | −1,6 |
|  | 300 | −43,0 | −44,1 | +16,6 | −46,9 | −2,5 |

*(Liver weight/body weight) × 100

TABLE 2

| | | 15 days treatment | | | | |
|---|---|---|---|---|---|---|
| Example n° | Dose mg/kg | Triglycerides | Total cholesterol | Cholesterol HDL | Cholesterol VLDL + LDL | Hepatic index* |
| 2 | 50 | −0,2 | −13,1 | −24,5 | −12,0 | +3,5 |
|  | 100 | −18,7 | −12,9 | −0,4 | −14,0 | −4,5 |
| 6 | 50 | −18,2 | −16,1 | +1,0 | −19,0 | −1,7 |
|  | 100 | −49,1 | −19,0 | +4,3 | −21,7 | −4,1 |
| 11 | 50 | −48,5 | −36,6 | −9,9 | −39,7 | +0,2 |
|  | 100 | −46,8 | −34,4 | +16,1 | −40,2 | −3,1 |
| 24 | 50 | −19,5 | −3,3 | −12,9 | −2,2 | +1,7 |
|  | 100 | −38,9 | −24,6 | −14,8 | −25,7 | −2,5 |
| 28 | 50 | −27,3 | −23,3 | +11,3 | −28,1 | +0,6 |
|  | 100 | −35,1 | −35,3 | +21,0 | −41,7 | −1,9 |
| 33 | 50 | −20,5 | −29,7 | +15,6 | −34,7 | +2,2 |

TABLE 2-continued

| | | 15 days treatment | | | | |
|---|---|---|---|---|---|---|
| Example n° | Dose mg/kg | Triglycerides | Total cholesterol | Cholesterol HDL | Cholesterol VLDL + LDL | Hepatic index* |
| | 100 | −30,6 | −33,8 | +19,4 | −39,7 | +3,9 |

*(Liver weight/body weight) × 100

TABLE 3

| Compound (example n°) | Dose mg/kg | Hepatic index* | Catalase enzyme activity umoli/min/mg proteins |
|---|---|---|---|
| Solvent | — | 5,4 | 539,8 |
| 2 | 300 | 6,0 | 603,0 |
| 6 | 300 | 5,9 | 504,6 |
| 11 | 300 | 5,8 | 444,7 |
| 24 | 300 | 6,1 | 438,3 |
| 28 | 300 | 5,6 | 479,7 |
| 33 | 300 | 5,3 | 378,5 |
| Clofibrate+ | 200 | 7,0 | 680,9 |

*(Liver weight/body weight) × 100
+Known compound having hypolipaemizing activity, used as standard at a pharmacologically active and hepatotoxic dosage The compounds of the present invention are characterized by a very interesting hypolipaemizing activity since it influences both the triglycerides and the cholesterol and, as regards the latter parameter, cause both the fraction related to the HDL and the fraction related to VLDL and LDL to be modified in a positive sense: this wide spectrum of activity is rather rare in the actually used hypolipaemizing agents. Moreover it is worth to point out that these compounds don't induce macroscopical side effects at the general level and don't induce hypertrophy and toxicity at the liver level, which is a target organ for a number of known hypolipaemizing compounds.

For the use as hypolipaemizing drug the compounds of the present invention are preferably administered by oral route.

The novel compounds thus can be prepared in form of capsules, tablets, pill, powders or liquid solutions or suspensions for oral use. All these pharmaceutical preparations contain the conventional additives and excipients.

The dosage of the compound to be administered for the hypolipaemizing therapy shall depend on the type of compound being used., on the weight of the patient and on the pathology to be treated. Generally it is considered that the daily dosage may vary between 200 and 2000 mg of active ingredient divided in 2 to 3 administrations. The compositions shall generally contain 100 to 1000 mg of active ingredient for unit dose.

We claim:

1. A compound represented by the following formula I:

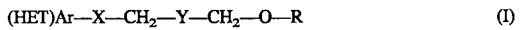

(HET)Ar—X—CH$_2$—Y—CH$_2$—O—R    (I)

wherein:

(HET) Ar represents a bicyclic nucleus consisting of fused 6-5 membered rings, the 6-membered ring containing 2 nitrogen atoms in the relative positions 1–3, the 5-membered ring containing two nitrogen heteroatoms also in the relative positions 1–3, the bicyclic nucleus bearing one to three substituents, identical to or different from each other, selected from the group consisting of straight chain $C_1$–$C_5$ alkyl, branched chain $C_1$–$C_5$, alkyl, NH$_2$, —OH, lower alkoxy, phenyl, and halogen, X represents —S—;

Y represents —CO—, —C=N—R$_2$, in which R$_2$ is OH, an alkoxy having 1 to 10 carbon atoms, aryloxy, arylalkoxy, —NH$_2$, —NHCONH$_2$, —NHCSNH$_2$; and R represents a phenyl substituted at para position with a carboxyl or a ($C_1$–$C_{20}$) alkoxycarbonyl group in which the alkoxy group is linear or branched.

2. A compound according to claim 1, wherein said (HET)Ar group is selected among theophilline, xanthine, guanine, caffeine, adenine and adenosine.

3. A compound according to claim 1, selected from the group consisting of 8-substituted nucleoside and purine derivatives having the formula (II) and (III):

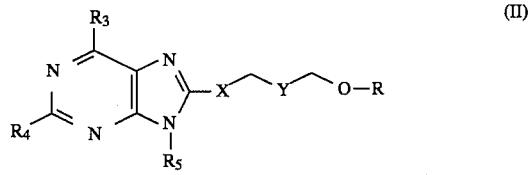

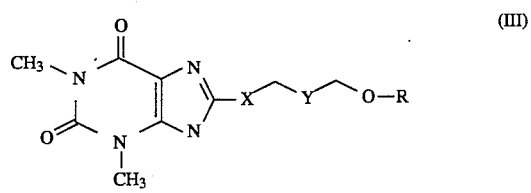

wherein

R$_3$ represents an amino group or a hydroxy group in equilibrium with the corresponding carbonyl form;

R$_4$ is a hydrogen atom or an amino group;

R$_5$ is a hydrogen atom or beta-D-ribofuranosyl radical in which both the primary hydroxy group at 5' and the two secondary hydroxy groups at 2' and 3' can be substituted with an acyloxy group in which the acyl derives from an aliphatic, aromatic or heterocyclic carboxylic acid, with a carbamyloxy group or with a mono- di- or tri-phosphate;

R is a phenyl substituted at the para position with a carboxyl or ($C_1$–$C_{20}$)alkoxycarbonyl group, wherein the alkoxy group is linear or branched, X is —S—

Y is —CO—, or C=N—R$_2$, wherein R$_2$ is as above defined.

4. A compound according to claim 3, wherein R$_3$ is an amino group and R$_4$ is a hydrogen atom, or R$_3$ is a hydroxy group in keto-enolic equilibrium, and R$_4$ is an amino group, R$_5$ is is a hydrogen atom or a beta-D-ribofuranosyl radical wherein the hydroxy groups are unsubstituted or substituted as above described, R is as above defined and X and Y are as before stated.

5. A compound according to claim 4, wherein R$_3$ is an amino group, R$_4$ is a hydrogen atom, R$_5$ is a hydrogen atom or a beta-D-ribofuranosyl radical wherein the hydroxy groups are unsubstituted or substituted as above described, R is as above defined and X and Y are as before stated.

6. A pharmaceutical composition comprising a compound selected among the compounds of claim 1, together with one or more vehicle and/or excipient.

7. A pharmaceutical composition according to claim 6, wherein said compound is selected among the compounds of formula (II) and (III).

8. A pharmaceutical composition according to claim 6 having hypolipaemizing activity.

9. A compound according to claim 1, selected from the group consisting of:
8-[3-[(p-isobutyloxycarbonyl)-phenoxy]-2-oxo-propylthio]-theophylline;
8-[3-[(p-carboxy)-phenoxy]-2-oxo-propylthio]-adenine;
8-[3-[(p-isobutyloxycarbonyl)-phenoxy]-2-hydroxy-propylthio]-caffein;
7-methoxymethyl-8-[3-[(p-isobutyloxycarbonyl)-phenoxy]-2-hydroxy-propylthio]-theophilline;
8-[3-[(p-isobutyloxycarbonyl)-phenoxy]-2-hydroxy-propylthio]-theophilline;
8-[3-[(p-isobutyloxycarbonyl)-phenoxy]-propylthio]-adenosine;
8-[5-[(p-isobutyloxycarbonyl)-phenoxy]-pentylthio]-adenosine;
8-[2-[(p-isobutyloxycarbonyl)-phenoxy]-ethylthio]-adenosine;
8-[3-[(p-isobutyloxycarbonyl)-phenoxy]-2-oxo-propylthio]-adenosine;
8-[3-[(p-carboxy)-phenoxy]-2-oxo-propylthio]-adenosine;
8-[3-[(p-isobutyloxycarbonyl)-phenoxy]-2-oxo-propylthio]-adenine;
8-[3-[(p-isobutyloxycarbonyl)-phenoxy]-2-hydroxyimino-propylthio]adenosine;
8-[3-[(p-isobutyloxycarbonyl)-phenoxy]-2-methoxyimino-propylthio]adenosine;
8-[3-[(p-isobutyloxycarbonyl)-phenoxy]-2-hydrazonecarboxamidepropylthio]-adenosine;
8-[3-[(p-isobutyloxycarbonyl)-phenoxy]-2-(R)-hydroxy-propylthio]-2',3'-O-isopropyliden-adenosine; and
8-[3-[p-(2,3-dihydroxy-propyloxycarbonyl)-phenoxy]-2-hydroxypropylthio]-adenosine.

* * * * *